United States Patent
Fujii et al.

(10) Patent No.: US 7,961,933 B2
(45) Date of Patent: Jun. 14, 2011

(54) METHOD OF SETTING REFERENCE DATA FOR INSPECTION OF FILLETS AND INSPECTION DEVICE USING SAME

(75) Inventors: Yoshiki Fujii, Nagaokakyo (JP);
Yasutomo Doi, Fukuchiyama (JP);
Akira Nakajima, Otsu (JP); Toshihiro Moriya, Nara (JP); Yasuaki Nakajima, Takatsuki (JP)

(73) Assignee: OMRON Corporation, Kyoto (JP)

( * ) Notice: Subject to any disclaimer, the term of this patent is extended or adjusted under 35 U.S.C. 154(b) by 997 days.

(21) Appl. No.: 11/880,169

(22) Filed: Jul. 20, 2007

(65) Prior Publication Data
US 2008/0040058 A1 Feb. 14, 2008

(30) Foreign Application Priority Data
Aug. 11, 2006 (JP) .................................. 2006-220689

(51) Int. Cl.
*G06K 9/00* (2006.01)
(52) U.S. Cl. ....................................... 382/145; 382/141
(58) Field of Classification Search .................. 382/145, 382/141
See application file for complete search history.

(56) References Cited

U.S. PATENT DOCUMENTS
2004/0101190 A1* 5/2004 Maida et al. .................. 382/150
2005/0196996 A1* 9/2005 Yamasaki et al. ............. 439/329

FOREIGN PATENT DOCUMENTS
JP 63-112054 11/1989
JP 10-118641 11/1999
JP 2002-228181 3/2004

* cited by examiner

*Primary Examiner* — Vikkram Bali
*Assistant Examiner* — Haris Bajwa
(74) *Attorney, Agent, or Firm* — Weaver Austin Villeneuve & Sampson LLP

(57) ABSTRACT

Reference data for automatically inspecting shapes of fillets formed on a substrate are set to an inspection device that illuminates the substrate from specified directions to generate an image. For each type of components mounted to the substrate, a database is prepared, registering sets of reference data corresponding to different fillet shapes in correlation with heights of solder for forming fillets having these shapes. After components to be an object of inspection are identified, specified steps are carried out on each of these components, including the step of obtaining data on the height of solder for forming the fillet related to a land for which a target area for inspection has been set and reading out reference data corresponding to the data obtained from the reference data registered in the database.

8 Claims, 7 Drawing Sheets

| | FILLET TYPE | FILLET SHAPE | IMAGE | Threshold deriving rule for measurement value of blue area |
|---|---|---|---|---|
| SQUARE CHIP | SQUARE CHIP A | | | Width: 0.5x(Component width) Length: 0.6x(Component width) |
| | SQUARE CHIP B | | | Width: 0.5x(Component width) Length: 0.4x(Component width) |
| | SQUARE CHIP C | | | Width: 0.3x(Component width) Length: 0.5x(Component width) |
| | SQUARE CHIP D | | | Width: 0.5x(Component width) Length: 20μ(Component width) |
| IC | IC-A | | | Width: 0.5x(Component width) Length: 50μ(Component width) |
| | IC-B | | | Width: 0.1x(Component width) Length: 30μ(Component width) |
| | IC-C | | | Width: 0.3x(Component width) Length: 0.8x(Component width) |

BLUE AREA   RED AREA

*FIG. 3*

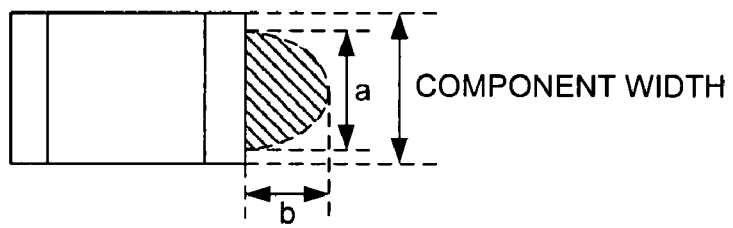

| FILLET TYPE | | IMAGE | SOLDER HEIGHT | WETTABILITY | LAND LENGTH | DISTANCE TO OPPOSITE LAND (FOR DISTINGUISHING SECONDARY REFLECTION) |
|---|---|---|---|---|---|---|
| SQUARE CHIP | SQUARE CHIP A | | 1/3 of component height or more | | 100μm or more | LM or more |
| | SQUARE CHIP B | | Less than 1/3 of component height | | 100μm or more | |
| | SQUARE CHIP C | | 1/3 of component height or more | | 100μm or more | less than LM |
| | SQUARE CHIP D | | | | Less than 100μm | |
| IC | IC-A | | 0.05mm or more | OK | | |
| | IC-B | | Less than 0.05mm | | | |
| | IC-C | | 0.05mm or more | NG | | |

METHOD OF SETTING REFERENCE DATA FOR INSPECTION OF FILLETS AND INSPECTION DEVICE USING SAME

This application claims priority on Japanese Patent Application 2006-220689 filed Aug. 11, 2006.

BACKGROUND OF THE INVENTION

This invention relates to a device for inspecting the external view of a substrate on which fillets are formed in a soldering process by obtaining its image while illuminating it from specified directions and using a regularly reflected optical image of the fillets in the generated image to automatically inspect the shape of each fillet. In particular, this invention relates to the technology of setting reference data necessary for the inspection of the fillets to such an inspection device.

Inspection devices of the type for automatically inspecting the external view of a substrate are usually provided with image taking means such as a camera and a line sensor and a controller incorporating a computer. The controller is adapted to take in an image of the target substrate to be inspected by the image taking means, to measure the positions and sizes of target portions to be inspected such as fillets and to judge whether the target portion is good (OK) or not good (NG) by comparing the obtained measured values with specified reference values for judgment.

The assignee herein is currently developing an automatic inspection device incorporating an optical system referred to as the Color Highlight system. As disclosed in Japanese Patent Publication Tokko 6-1173, the Color Highlight system is adapted to irradiate a substrate with red, green and blue light respectively from different angles to obtain an image representing the slope condition of a target portion for inspection (generally a soldered portion) by the distribution of the red, green and blue colors. An inspection device incorporating this Color Highlight system is adapted to judge whether fillets are normally formed or not by detecting areas of each color by means of a binarization process, measuring their positions and sizes and comparing them with reference value for judgment.

When such an inspection device is used to carry out an automatic inspection, various reference data for the inspection must be set and registered in the memory of the inspection device. In the above, the reference data are those that serve to indicate what method should be used how in what steps in order to inspect fillets that are the target portions to be inspected. They may be interpreted as data that represent various standards which must be referenced as a series of processes (such as generation of an image, extraction of target portions to be inspected, measurements and judgments) to be carried out for the inspection.

The aforementioned reference data include, for example, data required for setting a target area of inspection (the position and the size of the area), the kinds of process to be carried out for detecting a target portion to be inspected (such as binarization process, edge extraction process and projection process), methods of the measurement process for a target area for the inspection, and judgment reference value for determining whether the result of measurements was good or no good. If the detection of a target portion to be inspected is carried out by binarization, the threshold value for this binarization process is also included in the reference data.

According to the prior art process for setting reference data for inspection (or the so-called teaching process), an image is obtained of a model substrate with each target portion to be inspected in a good condition (hereinafter referred to as the "good model") and is displayed, and an inspector sets necessary reference data for each component while observing this displayed image.

It has also been known to preliminarily register standard reference data (so-called library data) for each component in order to reduce the workload for the setting of such reference data for inspection and to read out such library data to be set. Japanese Patent Publication Tokkai 2004-71781 discloses, for example, a process of generating reference data for inspection (referred to as the inspection data) by combining position data of a component read out from CAD data with library data.

According to Japanese Patent Publication Tokkai 11-311508, a specific threshold value for judgment is registered as library data for each component but it is also possible to register rules (referred to as the method of calculating inspection parameters) for obtaining a threshold value instead and to calculate a specific threshold value at the time of the teaching process by using the data on the shape of the component actually mounted to the substrate and the library data. In this way, since it becomes possible to register reference data for inspection common to all components of a same type, it becomes easier to change the rule for setting threshold value and to add new components with different sizes.

Since the shape of a fillet sometimes changes, depending on the height of the cream solder printed on the land prior to the soldering process, it may be difficult to maintain a high level of accuracy in the inspection if same reference data are used uniformly.

One of principal causes of fluctuations in the height of cream solder is in the structure (more particularly the thickness) of the metallic mask that is used in the solder printing process. Since the mask is designed according to the structure of the substrate, the height of the solder may vary even for the same component, depending on the substrate on which it is mounted.

Moreover, since fillets are formed between electrodes on the side of the component and lands, differences in the relative height of the solder with respect to the height of the component may affect the shape of the fillet in the case where the fluctuation in the size of component is large.

Consider a situation where two square chips with different component heights are mounted to a same substrate, and let us assume that the lands for mounting these components are the same in size and shape and that the shape and size of the opening of the masks used for the printing of cream solder are set identically for these lands. If this mask is used to print the cream solder on each land, these two square chips are thereafter mounted and the reflow process is carried out, the melted solder may rise nearly to the height of the upper surface of the electrode on the side of the component and a steep fillet will be formed by the higher square chip while the fillet formed by the lower square chip is sloped more gently.

SUMMARY OF THE INVENTION

It is therefore an object of this invention in view of the problem described above to automatically set reference data for inspection suitable for the actual shape of a fillet even where fillets change their shapes, depending on the height of the solder.

A method of this invention is for setting reference data to an inspection device for automatically inspecting shapes of fillets formed on a substrate by illuminating the substrate from specified directions to generate an image and using image of the fillet in this generated image. In this method, a database in which a plurality of sets of reference data corresponding to mutually different fillet shapes are registered in correlation with heights of solder for forming fillets of corresponding shapes is preliminarily prepared for each of component types. Next, design data of the substrate are used to identify components to be an object of fillet inspection and Step A, Step B, Step C and Step D to be explained below are carried out on each of these identified components.

In Step A, positions and sizes of lands corresponding to identified one of the components are identified. In Step B, a target area for inspection of fillets is set for each of the lands based on the identified positions and sizes. In Step C, data are obtained on the heights of solder for forming the fillets related to the land for which the target area for inspection has been set and reference data corresponding to the data obtained from the reference data registered in database are read out. In Step D, data required for setting the target area in Step B and the reference data read out in Step C are registered in correlation in a memory of the inspection device.

In Step A, the position and size of the land corresponding to an identified component may be directly read out from the design data of the substrate but it is not to limit the scope of the invention. For example, each land on the substrate may be detected from an image obtained from a bare board before cream solder is printed and position and size of the land closest to the target component being processed may be selectively measured. The position of the component when this process is carried out may be obtained from the design data of the substrate or the user's input of coordinates may be received.

It is preferable to have registered in the database to be used in this method at least the content of the measurement process to be carried out on fillets, as well as inspection reference data based on the knowledge and experience of a skilled person regarding the judgment threshold values for judging appropriateness of measured values obtained by such measurement processes. It is also preferable to register for each component type inspection reference data corresponding to a plurality of fillet shapes that can occur with that component type.

By such a method, inspection reference areas can be set based on the design data of the substrate, and inspection reference data suitable for the fillet shapes formed by solder can be set based on the height of solder of the land within these inspection reference areas.

In the method, the height of the cream solder applied to a land prior to the mounting of a component may be used as the height of solder for forming a fillet. In this case, the data indicating the height of solder may be obtained by measuring the height of cream solder by using a substrate for which the condition of printing was good in the solder printing process.

It is further preferable to use the height of solder when it is melted in the reflow process as the height of solder for forming a fillet. This is because the height of solder varies due to factors such as the size of the land, the height of the component and the surface tension of the solder if the reflow process is carried out although the height of cream solder becomes about the same for a same substrate since the thickness of the opening of the mask is approximately the same. It is difficult to measure the height of solder in this case but an approximate value can be obtained by a calculation as explained below.

For example, the size of the land a and the size of the opening of the mask b are read out of the design data of the substrate in Step C and the product of b with the preliminarily inputted thickness value c of the mask is divided with aforementioned value a to obtain $((b \times c)/a)$ as the height of solder for forming the fillet.

As a more preferable example, not only is the size of the opening of the mask read out of the design data of the substrate in Step C but also the same design data and the shape data of the target component being processed are used to obtain the size a1 of the portion of the land not having any component mounted thereto and the product of b with the preliminarily inputted thickness c of the mask is divided by a1 to obtain $((b \times c)/a1)$ as the height of the solder for forming the fillet.

The two calculations above are for obtaining the height of solder when it is melted on the assumption that the cream solder filling the opening part of the mask has melted and spread uniformly over the land. Since the height of cream solder can be obtained by these methods by a calculation even without a real substrate, it becomes easier to set the inspection reference data.

By either of these calculations, it may be taken into consideration that the volume of cream solder becomes smaller when it is melted because flux is evaporated. Thus, the value obtained by these calculations may be multiplied by a specified rate of shrinkage to obtain the height of solder.

According to a preferred way of carrying out Step C when a component of a specifically identified type is to be processed, the height of an identified component is read out from a component database registering the height of each component of this type in Step A and the relative height of solder with respect to the height of the component that has been read out as data showing the height of solder for forming the fillet. By this method, even in the case of a component type such as square chips that have large variations in the size, it is possible to set a suitable inspection reference data value based on the relative height of solder with respect to the component that is mounted.

This invention is applicable also when different inspection reference data must be set for other factors although the height of solder for forming fillet is about the same. For example, if there are components of a type for which the probability is high that the reflection image of a fillet may include effects of so-called secondary reflection from a fillet on a neighboring component, the database may register, for such component type, reference data for inspection each for situations where secondary reflection is present and is not present. In Step C, furthermore, when a component of a type for which reference data are registered each for presence and absence of secondary reflections and when a plurality of reference data for inspection exist corresponding to the obtained height of fillet, design data of the substrate are used to calculate the distance between a land of the target component being processed and another land on an adjacent component opposite this land. The inspection reference data to be read out of the database are determined according to the result of comparison between the calculated distance and a specified threshold value.

By this method, inspection reference data can be automatically set with the effects of secondary reflection taken into consideration even in the case of a component type (such as square chips) with the possibility that the reflected image of a fillet may become different from a normal condition due to secondary reflection, although there may be no problem with the actual shape of the fillet.

As another example, the database registers, regarding component types for which fillet shape is likely to change depending on wettability of electrodes, reference data for inspection corresponding respectively to cases where wettability is good and not good for each range of solder height. In Step C, when components of a type for which reference data for inspection are registered respectively for good wettability and no good wettability are being processed and when there are a plurality of reference data for inspection corresponding to obtained height of fillet, data on wettability of the components obtained and reference data for inspection corresponding to the obtained data are read out from the database.

By this method, inspection reference data can be adjusted according to wettability for components of the type (such as ICs) for which shapes of the fillets change significantly according to the wettability of the electrode parts. Data on the condition (good or no good) of wettability may be obtained by a manual operation of the user. Alternatively, a table may be preliminarily prepared by correlating an electrode material database registering the materials of electrodes for each component and the relationship between each type of electrode material and wettability. With such a table, data on conditions of wettability can be obtained by identifying an electrode material from the electrode material database.

A device of this invention is for photographing a substrate with fillets formed thereon while illuminating from specified directions and automatically inspecting the shape of the fillet by using its reflected image in a generated image and may be characterized as comprising a database registering for each of component types a plurality of kinds of reference data for inspection corresponding to different shapes of fillets in correlation with ranges in height of solder for forming fillets having corresponding shapes, reference data setting means for setting reference data for inspection for each of components on a target substrate for inspection and a memory for storing the reference data for inspection set by the reference data setting means. The reference setting means includes component identifying means for identifying a component of which fillets are inspected and component type thereof, land identifying means for identifying position and size of lands corresponding to the identified component which was identified by the component identifying means, area setting means for setting a target area for inspecting a fillet for each of the lands for which position and size were identified by the land identifying means, based on the identified position and size, data extracting means for obtaining data indicative of height of solder for forming a fillet regarding the land for which target area for inspection was set, and reading out reference data for inspection corresponding to the data obtained from the reference data for inspection of the target component registered in the database, and registering means for registering in the memory, for the target area for inspection set by the area setting means, data required for setting the target area for inspection and the reference data for inspection read out by the data extracting means in correlation.

With a device thus structured, the database registering the reference data for inspection is preferably contained in the memory of a substrate inspection device but this is not a requirement. A removable memory medium such as a CD-ROM may be used, or it may be provided through communication with an external apparatus.

In summary, this invention makes it possible to automatically set reference data for inspection suitable for the shape of the fillet by using a database, based on the height of solder for forming that fillet. Thus, the capability of automatically setting reference data for inspection can be improved significantly and the reference data thus set can be used to carry out an inspection of a high level of accuracy.

BRIEF DESCRIPTION OF THE DRAWINGS

FIG. 3 shows the structure of an example of inspection reference database.
FIG. 4 is a drawing for explaining the concepts of the width of a component and the width and the length of a fillet.
FIG. 5 shows an example of judgment reference table.

DETAILED DESCRIPTION OF THE INVENTION

Figure 1:
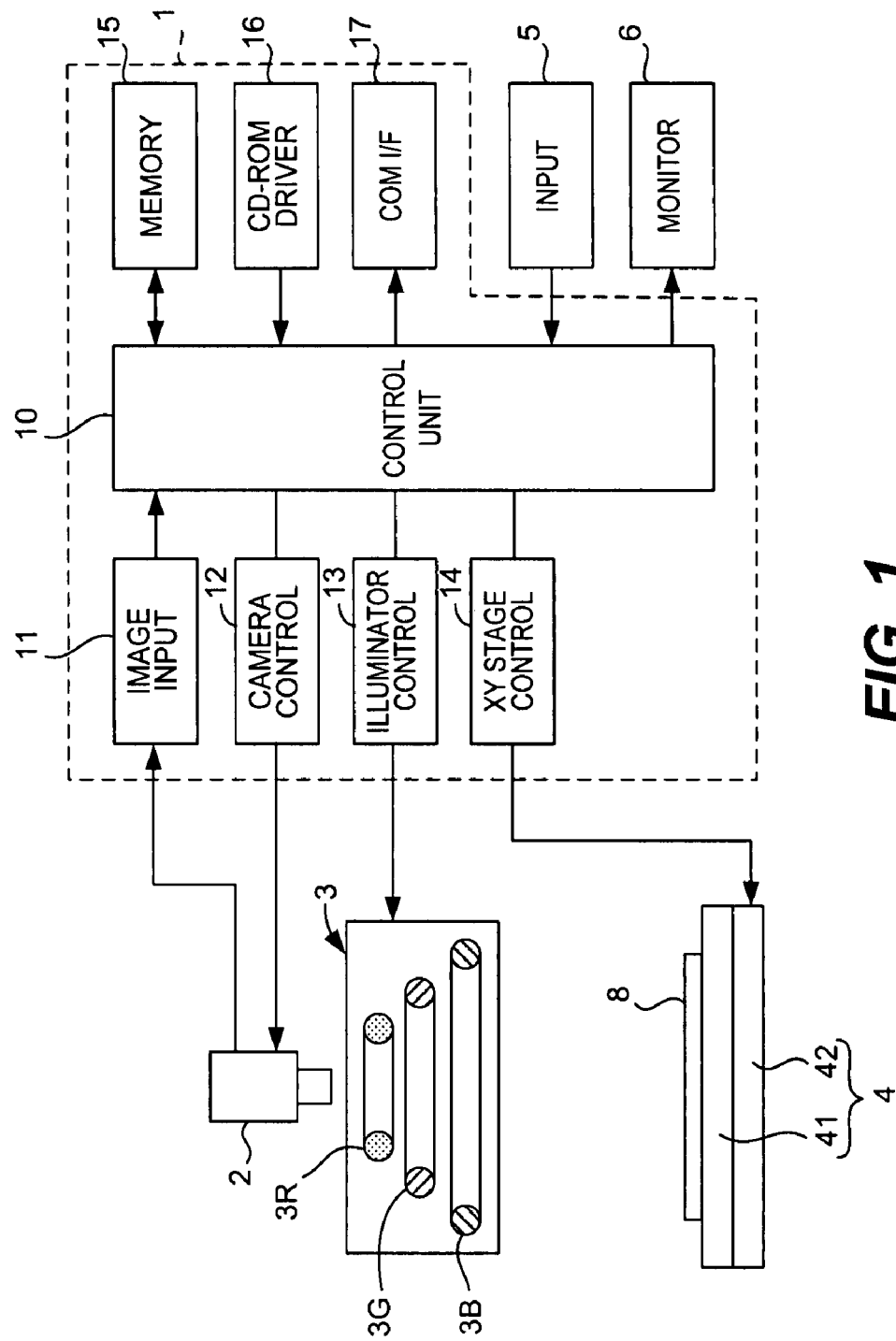
FIG. 1 is a structural block diagram of an inspection device embodying this invention.

FIG. 1 is a structural block diagram of an inspection device for using this invention. This inspection device is for inspecting the fillet of each component mounted to a substrate after it has gone through the reflow process and is provided with a controller 1, a camera 2, an illuminator 3, a substrate stage 4, an input device 5 and a monitor 6.

The substrate stage 4 includes a table 41 for supporting a substrate 8 and a moving mechanism 42 including an X-stage and a Y-stage (not shown).

The camera 2 and the illuminator 3 form an optical system of the Color Highlight type as disclosed in Japanese Patent Publication Tokko 6-1173. The camera 2 is for producing still color images and is set above the substrate stage 4 with its image taking surface facing downward and its optical axis oriented vertically.

The illuminator 3 is comprised of three annular light sources 3R, 3G and 3B provided between the substrate stage 4 and the camera 2. These annular light sources 3R, 3G and 3B are for emitting red, green and blue light, respectively, disposed with their centers on the optical axis of the camera 2, and have different diameters so as to be able to irradiate the substrate 8 from different directions.

The controller 1 is provided not only with a control unit 10 comprising a computer but also with an image input part 11, a camera control part 12, an illuminator control part 13, an XY stage control part 14, a memory 15, a CD-ROM driver 16 and a communication interface 17.

The image input part 11 includes an interface circuit for the camera 2. The camera control part 12 is for outputting a timing signal to the camera 2 for ordering it to obtain an image.

The illuminator control part 13 controls the switching on and off of each of the light sources 3R, 3G and 3B of the illuminator 3 and adjusts the quantities of light. The XY stage control part 14 controls the timing of motion and the distance of displacement of the substrate stage 4.

The memory 15 stores not only programs for inspection but also a reference database 101 and a component shape database 102 (to be described below), as well as an inspection data file 103 generated by using these databases 101 and 102. For each component, the inspection data file 103 registers reference data that are necessary for inspecting the fillets of that component. When the substrate 8 is divided into a plurality of areas to obtain its images, the inspection data file 103 also registers such data that are necessary for matching the field of vision of the camera 2 at each of the target image-taking positions (such as the distances by which the substrate stage should be moved).

The control unit 10 serves to position the camera with the substrate 8 by controlling the motion of the substrate stage 42 through the XY stage control part 14 and to take images. The color image thus taken is inputted to the control unit 10 through the image input part 11 and stored in its internal memory (such as a RAM). For each component in the color image thus stored in the RAM, the control unit 10 carries out inspection of fillets sequentially by using the reference data registered in the inspection data file 103.

The control unit 10 further serves to transmit the results of measurement and judgment on each component as well as the images used for the inspection through the communication interface 17 to a data processor.

Figure 2:
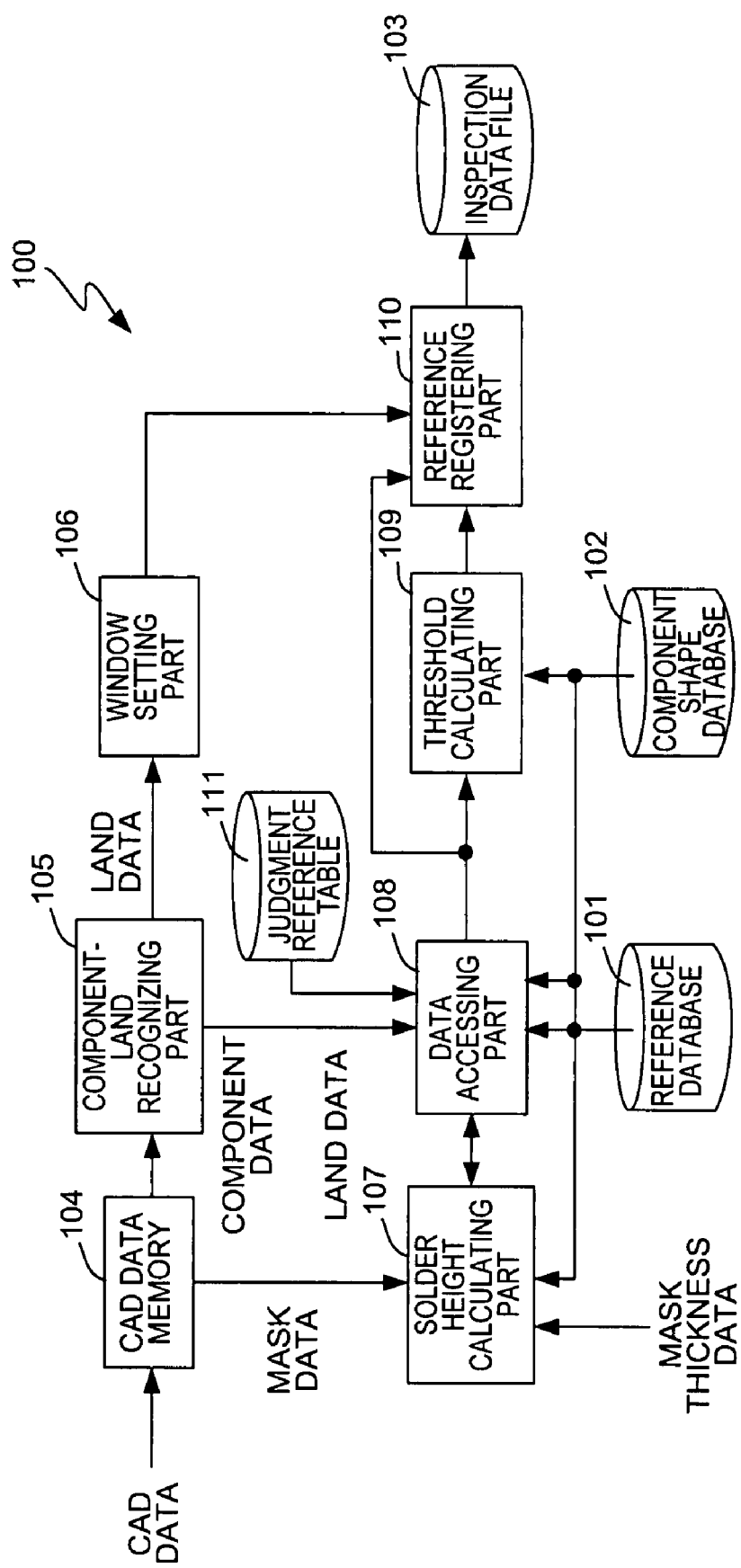
FIG. 2 is a functional block diagram of an inspection reference setting system of this invention.

With an inspection device of this kind, there are frequently situations where an image is obtained, as a teaching process, of a model substrate with fillets of its components all in a good condition and the image thus obtained is used to create reference data for inspection. With the inspection device of this invention, however, the reference database 101, the component shape database 102 registering the shapes of various components, CAD data of the substrate, etc. are used to automatically set various kinds of reference data without the necessity of obtaining the image of a model substrate. For the purpose of thus automatically setting reference data, the controller 1 of the inspection device incorporates a reference setting system 100, which is provided, as shown in FIG. 2, not only with the reference database 101, the component shape database 102 and the inspection data file 103 as described above, but also with a CAD data memory 104, a component-land recognizing part 105, a window setting part 106, a solder height calculating part 107, a reference data accessing part 108, a threshold calculating part 109, a reference registering part 110 and a judgment reference table 111.

Of the components of the reference setting system 100 described above, the CAD data memory 104, the reference database 101, the component shape database 102, the inspection data file 103 and the judgment reference table 111 are each set within the memory 15 of the controller 1. The other components are functions set in the control unit 10 by a program installed in the memory 15.

Data that are read into this reference setting system 100 are used in the process for identifying the components mounted to the substrate as well as their kinds and the process for identifying the position and size of the land corresponding to each component. Explained more specifically, data on each component such as its mounting position, its type (or its common name such as square chip, IC and capacitor) and its article number are set, and data for representing the positions and sizes of lands (hereinafter referred to as the land data) are further set. Data showing the position and size of the opening of the metallic mask used in the solder printing process (hereinafter referred to as the mask data) are also set. The mask data are basically to be used in the cream solder printing process but they are used in the present embodiment of the invention by the solder height calculating part 107.

The CAD data are either read out of a CD-ROM set on the CD-ROM driver 16 or transmitted from an external device (not shown) and taken in through the communication interface 17 to be stored in the CAD data memory 104.

The reference database 101 and the component shape database 102 are pre-installed in the inspection device, but they are both adapted to be updated by means of the CD-ROM or through an external communication.

As will be explained in detail below, inspection reference data corresponding to a plurality of fillet shapes that can occur with each type of component are registered in the reference database 101. The types of component in the database are classified so as to match the types of components in the CAD data, and each type of component is assigned the same name as used in the CAD data.

Reference data for inspection corresponding to each shape of fillet include data for indicating the color detected from the image of the fillet, data for indicating the program to be executed for measurements or judgments (such as the file name of the program and the address for showing its stored position), and the rule for obtaining a threshold value for judgment (hereinafter referred to as the threshold deriving rule).

The component shape database 102 stores data for identifying each component such as its article number, the name of its type, the name of its maker and its model name, as well as the shape data of that component. Shape data are for expressing the size and shape of the component by specific numbers, and the longitudinal and transverse dimensions and height for the main body of each component are stored. Data which are peculiar to the type of component may also be stored. In the case of a component belonging to the category of IC, the pitch between lead lines, width of each lead line, distance between mutually opposite edges and the height of lead lines are stored.

The component-land recognizing part 105 is for recognizing each component mounted to the substrate separately, based on the names of types of components and article number (hereinafter referred to as the component data) in the CAD data. It further identifies the land corresponding to each component and obtains land data of each land. The window setting part 106 serves to take in land data corresponding to each component from the component-land recognizing part 105 and to set an inspection target area of a size that includes the land (hereinafter referred to as the land window), based thereon.

The component data and the land data are supplied to the reference data accessing part 108 from the component-land recognizing part 105. If the type of component which is the object of teaching or the size of the land is recognized in these data, the reference data accessing part 108 identifies the data matching the shape of the fillet formed on that land from the plurality of inspection reference data registered in the reference database 101 and reads out these identified data. The judgment reference table 111 is used in this process of identifying the inspection reference data. It also causes the solder height calculating part 107 to carry out the process of calculating the height of the solder on the land except for some of the components.

After the identified inspection reference data are read out of the reference database 101, the reference data accessing part 108 supplies the threshold deriving rule in these data to the threshold calculating part 109. The threshold calculating part 109 calculates the judgment threshold value for the inspection of fillet corresponding to the component which is the object of teaching by a calculating process using the shape data of the component in this threshold deriving rule.

The reference registering part 110 takes in various inspection reference data including the aforementioned threshold value for judgment, receives from the window setting part 106 those data that are necessary for setting the land window (which are data showing the position and size of window hereinafter referred to as the land window setting data), and stores them in inspection data file 103 by correlating them.

Binarized threshold values for detecting each of the red, green and blue colors are also stored in the inspection data file 103 as inspection reference data common to all components. These binarized thresholds are also registered in the reference database 101 and are read out and stored in the inspection data file 103 by a processing part (not shown).

Although an example was shown above wherein data showing the type of component are in the CAD data, if CAD data not containing such data are used, data on the type of component are separately inputted by the user and such data inputted by the user are supplied to the component-land recognizing part 105.

Next, specific details of inspection reference data and processes for setting them are explained for the case of square chips and ICs as principal examples of type of components.

FIG. 3 shows an example of data structure registered in the reference database 101 regarding these two types of components. In this example, shapes of fillets which appear in each of these two types of components are classified into a plurality of types (hereinafter referred to as the fillet types) and individual inspection reference data are set to each of these fillet types.

Although fillet types are given names including names of the component type such as "Square chip A" and "IC-A", it should be remembered that fillet types are not for classifying components but for classifying the shapes of fillets. In other words, fillets of all fillet types may be formed to any of components of the same component type. Similarly, as will be explained below, there may be situations where same components have different fillet types, depending on the lands.

Although inspection reference data include aforementioned plurality of kinds but FIG. 3 is limited to the threshold deriving rule. Although Color Highlight inspecting devices of recent years are adapted to always detect blue areas while green and red areas are also detected if necessary, it is assumed for convenience in this example that only blue areas are to be detected and a threshold deriving rule related to measured values for blue areas is shown.

Of the data shown in FIG. 3, the essential data for the reference database 101 are the fillet type name and threshold deriving rule. Fillet shapes and images are for showing specific details of each type and they are not necessary to register in the reference database 101. They may be recorded, for example, in a file other than the reference database 101 such that the user can reference them.

"Fillet shape" is a chart showing the cross-sectional shape of the fillet. "Image" is a chart of the fillet in the image obtained by the Color Highlight optical system and the portion corresponding to the fillet is colored in blue and red according to the actual color distribution. In FIG. 3, blue areas are indicated by a pattern of diagonal lines and red areas are indicated by a dotted pattern. Green areas are so small that they are not included.

As "Threshold deriving rule," rules for obtaining threshold values for measured values for the width and length the fillet (hereinafter referred to as fillet width and fillet length) are set in this example. Since rules of multiplying the width of the component or the component of the lead line with a specified factor are set except for some types of components, different threshold values are set, depending on components.

FIG. 4 shows how fillet width and fillet length are defined in the case of a square chip. In the case of a square chip, "component width" is its width in the direction perpendicular to the direction in which the electrodes are arranged (or the vertical direction in the figure). "Fillet width" is the largest value "a" of the length of the blue area in the direction of the component width, and "fillet length" is the largest value "b" of the length of the blue area in the direction perpendicular to the component width. The case of an IC is not illustrated but the fillet width is similarly the largest value of the length of the blue area in the direction of the width of the lead line, and the fillet length is the largest value of the length of the blue area in the direction along the length of the lead line.

Next, the relationship between the fillet shape and the threshold deriving rule of each type of component is explained. Regarding the square chips, although there are four fillet types that are set, Square chips A and C have nearly the same fillet shape. In these types, a steep fillet is formed starting from a relatively high point on the component (the upper edge in the illustrated examples). Square chip B is similar to Square chips A and C regarding the fillet length but since the starting point of the fillet is relatively low, the slope of the fillet becomes gentler. Thus, a red area appears near the tip on the image of the fillet.

Square chips A and C are distinguished by the presence and absence of secondary reflection. Secondary reflection means the situation where reflected light from the fillet on an adjacent component in a mutually facing relationship is irradiated and this irradiated light is being reflected. It is known that secondary reflection is likely to occur if a fillet is steep and the distance to the adjacent fillet is small. In the present example, the type without the occurrence of secondary reflection is referred to as Square chip A and the type with secondary reflection is referred to as Square chip C. The image of a fillet corresponding to Square chip A becomes nearly entirely blue but a red area caused by secondary reflection appears inside the blue area in the image of a fillet corresponding to Square chip C.

Against these three types, Square chip D corresponds to a fillet which is short and steep because the land is extremely small. The image of a fillet of this type becomes nearly entirely blue, like that of Square chip A except that the fillet length becomes much smaller than that of Square chip A.

These differences in the images are reflected in the threshold deriving rules of different types. Explained more in detail, a value corresponding to 0.5 times the component width is set as the threshold value for the fillet width and a value corresponding to 0.6 times the component width is set as the threshold value for the fillet length in the case of Square chip A. For Square chip B, the threshold value of the fillet width is set to be the same as for Square chip A, but the threshold value for the fillet length is set to be smaller than for Square chip A by taking into consideration the presence of the red area. As for Square chip C, the threshold value is made smaller than for Square chip A regarding both the fillet width and length by taking into consideration the occurrence of secondary reflections.

As for Square chip D with a fillet that is steep and short, the threshold for fillet width is set as for Square chip A but the threshold for fillet length is fixed (20 µm). This is because it is experimentally known that fillets of this type take on nearly the same shape independently of the height of the cream solder before it becomes a fillet.

As for the three types of IC, IC-A corresponds to a steep fillet. In the case of this type, an image is obtained with the fillet nearly entirely becoming blue, as in the case of Square chip A.

A fillet corresponding to IC-B, on the other hand, slopes gently, starting from a relatively low position on the electrode. On the image of a fillet of this type, a red area becomes more distinctive. The direction of the width becomes almost all red in portions corresponding to the tip of the fillet.

A fillet corresponding to IC-C is deformed into a shape which is flat at the center and sloped portions are few. Such deformation of the fillet occurs when the wettability of the lead line (or the mounted condition of the solder with respect to the lead line) is poor, say, because a palladium plating layer is formed on the surface of the lead line. Red areas appear on the image of a fillet of this type along the direction of its length.

In the threshold deriving rules for the IC, too, the threshold values for judgment are made different for different types according to the difference in their images as explained above. Explained more in detail, the threshold values for judgment of fillet width are made smaller for IC-B and IC-C than that for IC-A. The threshold values for fillet length are fixed (50 μm and 30 μm) for IC-A and IC-B but that for IC-C is varied according to the length of the land.

The judgment reference table 111 stores data as shown in FIG. 5 for judging to which of the types described above the fillet of the target component corresponds. The figures in the column entitled "Image" are displayed merely for being referenced and need not actually be stored in the table.

Data that correlate the fillet type set in the reference database 101 with the height of the solder for forming the fillet (hereinafter referred to as the solder height) are set in the judgment reference table 111. The solder heights of Square chips A, B and C are each represented as a numerical range of ratio of the height of solder with respect to the component, and the solder heights of IC-A, IC-B and IC-C are each represented as a specific numerical range. For Square chip D for which the solder height need not be considered, NULL is entered as the solder height.

The data on the four types of square chips include the lengths of the corresponding lands (hereinafter referred to as the land lengths). The data on Square chips A and C include a parameter for distinguishing the presence and absence of secondary reflection (or the distance between the land where the fillet is formed and the land of the component adjacent and opposite thereto). As for the ICs, the data on IC-A and IC-C include data item indicating whether the wettability of the lead line is good or no good.

The reference database 101 shown in FIG. 3 and the judgment reference table 111 shown in FIG. 5 are linked through the name of the fillet type. Through this link, the inspection reference data of each type except Square chip D are correlated to a range in the height of solder related to the formation of a fillet having the corresponding shape. Thus, if the height of solder formed on an actual land is known, it is possible to identify the inspection reference data corresponding to this height.

Although the same range of height is assigned to Square chips A and C and to IC-A and IC-C, FIG. 5 shows that Square chips A and C can be distinguished by the distance to the opposite land and IC-A and IC-C can be distinguished by the condition of wettability. Square chip D for which the solder height is not correlated can also be distinguished from the other three types by the land length.

Figure 6:
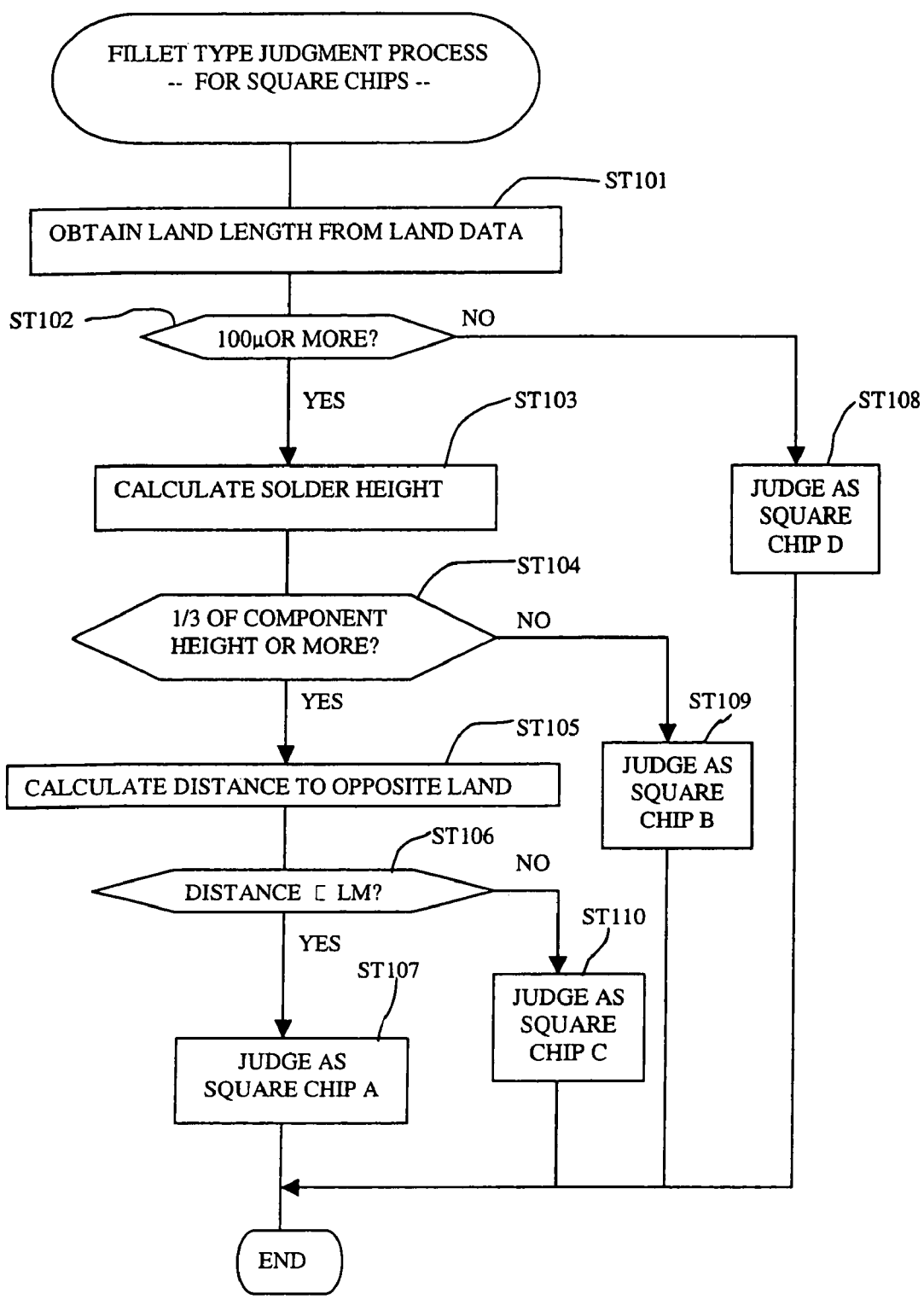
FIG. 6 is a flowchart of the process for judging the fillet type for a square chip.
Figure 7:
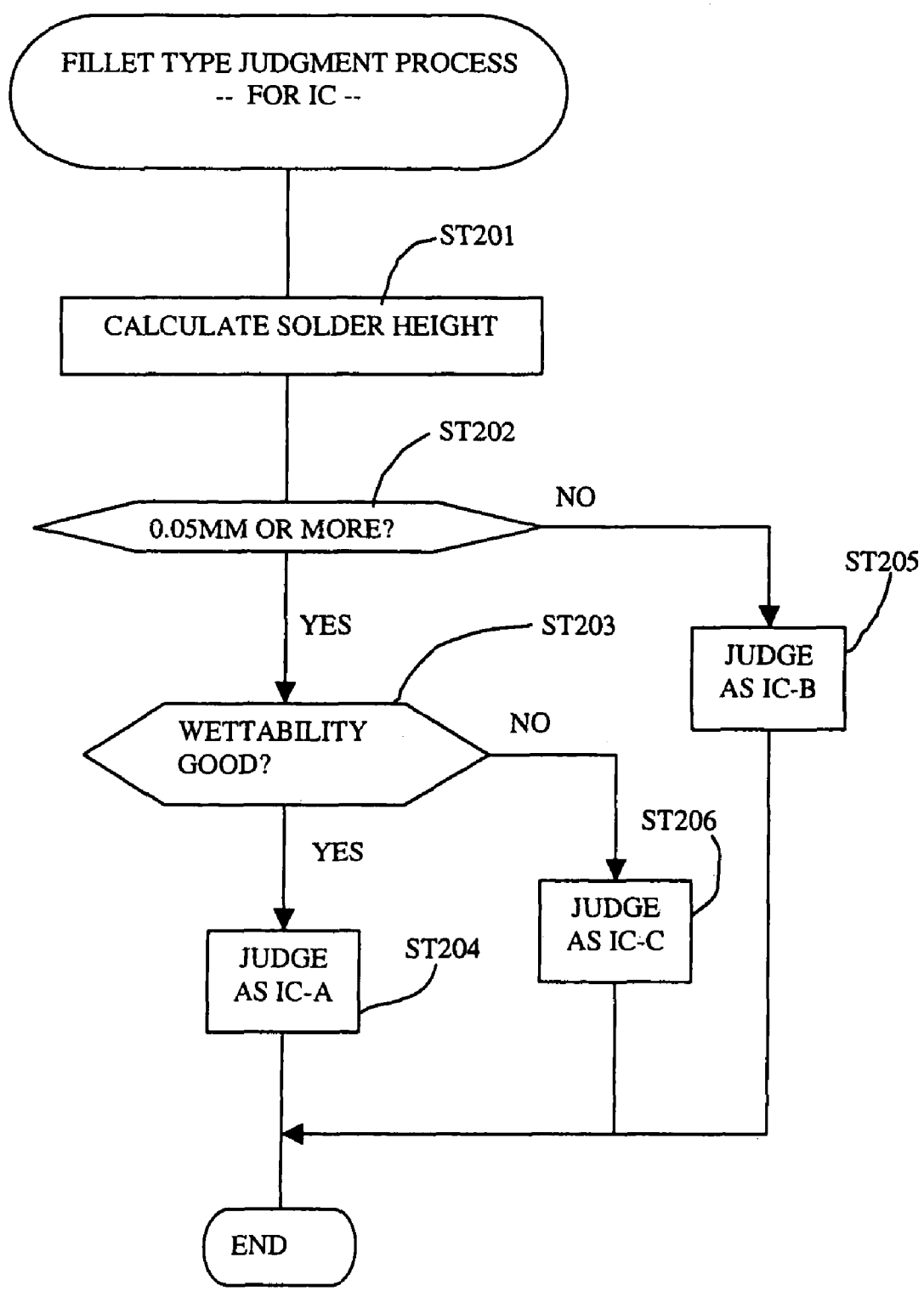
FIG. 7 is a flowchart of the process for judging the fillet type for an IC.

FIG. 6 shows the steps of the process when the fillet type of a square chip is determined and FIG. 7 shows the steps of the process when the fillet type of an IC is determined. In what follows, these processes are explained with reference to FIG. 5.

The judgment process for a square chip of FIG. 6 starts by obtaining the land length from the land data on the target land being considered in the CAD data (Step ST101) and checking whether or not it is 100 μm or greater (Step ST102). According to FIG. 5, Square chips A, B and C all correspond to a land length of 100 μm or greater but the land length corresponding to Square chip D is less than 100 μm. Thus, the fillet type can be determined as Square chip D (Step ST108) if it is NO in Step ST102.

If the land length is 100 μm is more (YES in Step ST102), the functions of solder height calculating part 107 are employed to calculate the height of the solder (Step S103) as follows.

Firstly, the land data and the component data in the CAD data are used to obtain the area of the land and the center position of the component, and data on the sizes of the component main body and the electrodes are read out of the component shape database 102. These data are used to obtain the size SA of the target solder printing area on the land (the portion not overlapping with the electrodes). The area SB of the opening of the mask is extracted from the CAD data, and the thickness δ of the mask is separately inputted by the user. These data are used together to calculate as follows:

$$(\text{Solder height})=(SB)\delta/(SA). \tag{1}$$

This equation is for calculating the height of melted solder on the assumption that the cream solder buried in the opening part of the mask is melted and spreads uniformly all over the portion of the land not overlapped with the electrodes. However, since the cream solder comprises solder particles contained in flux, its volume decreases as it melts because of the evaporation of the flux. Thus, the result of the calculation according to (1) may be multiplied by the ratio of shrinkage due to this decreased volume to obtain the height of the solder.

Next, the height of the object component of teaching is read out of the component shape database 102 and it is checked whether or not the solder height calculated in Step ST103 is ⅓ of this component height or more (Step ST104). According to FIG. 5, the solder height corresponding to Square chips A and C is ⅓ of the component height or more but the solder height corresponding to Square chip B is less than ⅓ of the component height. Thus, it is concluded that the fillet type is Square chip B (Step ST109) if it is NO in Step ST104.

If the solder height is ⅓ of the component height or more (YES in Step SDT104), the land data in the CAD data are used to calculate the distance to the land of the adjacent component in the mutually opposite relationship (Step ST105), and the calculated distance is compared with a specified value LM (Step ST106).

According to FIG. 5, the distance to the opposite land is LM or more in the case of Square chip A not generating secondary reflection but this distance is less than LM in the case of Square chip B that generates secondary reflection. Thus, if the distance calculated in Step ST103 is LM or more (YES in Step ST106), the fillet type is judged to be Square chip A (Step ST107). If the distance calculated is less than LM (NO in Step ST106), the fillet type is judged to be Square chip C (Step ST110).

In the judging process for the IC, the solder height is calculated (Step ST201) and it is checked whether it is 0.05 mm or more (Step ST202). According to FIG. 5, IC-A and IC-C correspond to a solder height of 0.05 mm or more but the solder height corresponding to IC-B is less than 0.05 mm. Thus, if it is NO in Step ST102, the fillet type is judged to be 1C-B (Step ST205).

If the solder height is 0.05 mm or more, it is checked whether the wettability is good or no good (Step ST203). The data necessary for this checking are inputted preliminarily by the user. For example, a screen for asking whether palladium plating is effected on the IC mounted to the substrate is displayed and the reply inputted to this question is used in the judgment of Step ST203. If the wettability is judged to be good (YES in Step ST203), the fillet type is judged to be IC-A (Step ST204). If the wettability is judged to be no good (NO in Step ST203), the fillet type is judged to be IC-C (Step ST206).

Figure 8:
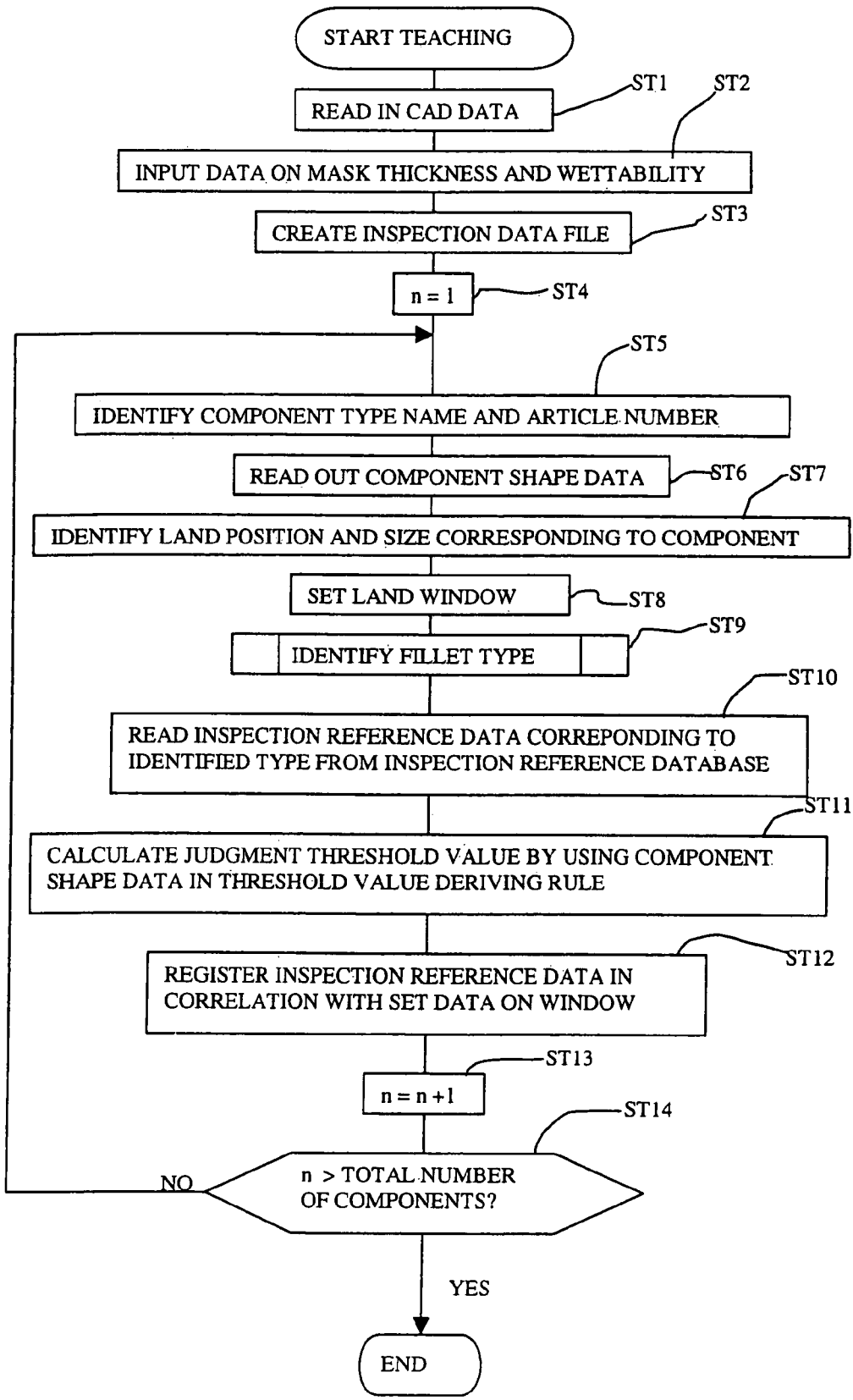
FIG. 8 is a flowchart of the teaching process for one substrate.

Next, the teaching steps are explained with reference to FIG. 8. To start, the CAD data of the object substrate of teaching are read (Step ST1). Next, the thickness of the mask used in the solder printing process and data related to the wettability of the lead lines of the IC are inputted (Step ST2) and the inspection data file 103 is created (Step ST3), except that the inspection data file 103 at this stage is empty, having only the file name set. Next, the counter n for counting the number of components is initialized to 1 (Step ST4) and the loop of Steps STY5-ST14 is subsequently repeated.

In this loop, the CAD data are used to identify the component type name and the article number of the component identified by the counter n (hereinafter referred to as the observed component) (Step ST5), and the component shape data of the observed component are read out of the component shape database 102 (Step ST6). The component shape data thus read out are stored in the work memory (RAM) within the control unit 10.

Next, the CAD data are used again to identify the position and size of the land corresponding to the observed component (Step ST7). Since a plurality of lands are usually identified in Step ST7, subsequent Steps ST8-ST12 are repeated for each of the identified lands although this is not shown exactly in FIG. 8.

For each of the identified lands, a land window with a size that includes that land is set (Step ST8). Next, a process for judging the fillet type corresponding to the type of the observed component is carried out (Step ST9). This is the process shown in FIG. 6 in the case of a square chip and the process shown in FIG. 7 if it is an IC. Next, inspection reference data corresponding to the fillet type determined in Step ST9 are read out for each land (Step ST10).

Next, numerical values of the component width and lead width for each land are read out of the component shape data and used in the threshold deriving rule in the inspection reference data read out in Step ST9 to calculate a specific threshold value for judgment (Step ST11). Inspection reference data inclusive of this threshold value are registered in the inspection data file 103 in correlation with the set data of land window (Step ST12). At this stage, the inspection reference data and the set data of land window are combined and inspection reference data in the final form with each assembly of combined data corresponding to one component are created and registered in the inspection data file 103.

Thereafter, the counter n is incremented (Step ST13) and the processes of Steps ST5-ST12 are repeated until the value of the counter n exceeds the total number of the components (YES in Step ST14).

Since Steps ST8-ST11 are executed for each of the identified lands, the sequence described above is applicable even in situations where different inspection reference data are applicable to different lands for the same component. In the case of a square chip where secondary reflection occurs with one fillet but it does not with another fillet, reference data of Square chip C are set for the former while those of Square chip A are set for the latter.

In situations where the relative height of solder varies with respect to the components due to different component sizes and the shapes and sizes of the lands and a plurality of different fillet shapes are expected due to such variations, the method of this invention described above makes it possible to automatically set inspection reference data for each land of an object component for teaching according to the shape of the fillet formed on that land. If the fillet shape changes for the same component, depending on the substrate on which it is mounted, the method makes it possible to set inspection reference data according to each fillet shape.

Also in situations where differences occur in the image of a fillet due to secondary reflection although there is no difference in the solder height or where differences occur in the fillet shape due to wettability of the electrode, the method of this invention makes it possible to set inspection reference data according to the condition of each fillet. This makes it possible to carry out an accurate inspection of fillets by using such set reference data.

Although an example was described above wherein the solder height is obtained by calculation, this is not intended to limit the scope of the invention. If cream solder applied to each land is to be inspected in the printing process of cream solder, the solder height measured in a solder printing process on a model substrate on which the condition of cream solder applied to all lands was good may be inputted and this inputted value or the numerical value obtained by multiplying this inputted value with a specified factor (which may be determined from the aforementioned shrinkage ratio caused by the evaporation of the flux) may be used as the solder height related to the formation of the fillet.

Moreover, although an example was described above wherein the binarization threshold values for the detection of colors of a fillet portion are set as common reference data, there are situations, depending on the component, where the shadow of a neighboring part may be cast on the fillet portion and common binarization threshold values cannot handle the condition. If such a condition can occur, it is preferable to identify fillets with a high probability of occurrence of a shadow based on the distances and positional relationships of components and to set different binarization threshold values for such fillets.

What is claimed is:

1. A method of setting reference data to an inspection device for automatically inspecting shapes of fillets formed on a substrate by illuminating said substrate from specified directions to generate an image and using image of said fillet in said generated image, said method comprising the steps of:

preparing, for each of component types, a database registering a plurality of sets of reference data corresponding to mutually different shapes in correlation with heights of solder for forming fillets of corresponding fillet shapes;

identifying components to be an object of fillet inspection; and carrying out Step A, Step B, Step C and Step D on each of said identified components; wherein:

said Step A is the step of identifying positions and sizes of lands corresponding to identified one of said components;

said Step B is the step of setting for each of said lands a target area for inspection of fillets based on the identified positions and sizes of lands;

said Step C is the step of obtaining data on the heights of solder for forming the fillets related to the land for which said target area for inspection has been set and reading out reference data corresponding to the data obtained from the reference data registered in said database; and said Step D is the step of registering data required for setting the target area in said Step B and the reference data read out in said Step C in correlation in a memory of said inspection device;

wherein design data of said substrate are used in the step of identifying components to be an object of fillet inspection, and said design data include data on the size of opening of mask for solder printing; and wherein said Step C further includes the steps of reading out from said design data the size of land and the size of said opening of said mask and calculating the height of solder for forming the fillet by dividing the product of an inputted value of thickness and the size of said opening of said mask by the size of said land.

2. The method of claim 1 wherein said Step C, when being carried out for a component of a specified type, includes the steps of:
reading out the height of the component identified in said Step A from a database that registers heights of components of said specified type; and
obtaining, as data on the height of solder for forming said fillet, relative height of solder with respect to the height of the component that was read out.

3. The method of claim 1 wherein:
said database registers, for each of component types with possibility of having an optical image caused by secondary reflection from a fillet of an adjacent component included in reflected image of fillet, reference data for inspection each for situations where secondary reflection is taking place and is not taking place; and
said Step C further includes the steps of:
using design data of said substrate, when component belonging to a component type for which reference data are registered each for presence and absence of secondary reflections and when a plurality of reference data for inspection exist corresponding to the obtained height of fillet, to calculate the distance between a land of the target component being processed and another land on an adjacent component opposite said land, comparing said calculated distance with a specified threshold value and determining reference data for inspection to be read out from said database based on the result of said comparing step.

4. The method of claim 1 wherein:
said database registers, regarding component types for which fillet shape is likely to change depending on wettability of electrodes, reference data for inspection corresponding respectively to cases where wettability is good and not good for each range of solder height; and
said Step C includes the steps, when components of a type for which reference data for inspection are registered respectively for good wettability and no good wettability are being processed and when there are a plurality of reference data for inspection corresponding to obtained height of fillet, of obtaining data on wettability of the components and reading out reference data for inspection corresponding to said obtained data from said database.

5. A method of setting reference data to an inspection device for automatically inspecting shapes of fillets formed on a substrate by illuminating said substrate from specified directions to generate an image and using image of said fillet in said generated image, said method comprising the steps of:
preparing, for each of component types, a database registering a plurality of sets of reference data corresponding to mutually different shapes in correlation with heights of solder for forming fillets of corresponding fillet shapes;
identifying components to be an object of fillet inspection; and
carrying out Step A, Step B, Step C and Step D on each of said identified components; wherein:
said Step A is the step of identifying positions and sizes of lands corresponding to identified one of said components;
said Step B is the step of setting for each of said lands a target area for inspection of fillets based on the identified positions and sizes of lands;
said Step C is the step of obtaining data on the heights of solder for forming the fillets related to the space for which said target area for inspection has been set and reading out reference data corresponding to the data obtained from the reference data registered in said database; and
said Step D is the step of registering data required for setting the target area in said Step B and the reference data read out in said Step C in correlation in a memory of said inspection device;
wherein design data of said substrate are used in the step of identifying components to be an object of fillet inspection, and said design data include data on the size of opening of mask for solder printing; and
wherein said Step C further includes the steps of reading out from said design data the size of said opening of said mask, obtaining the size of the portion of the land not having any component mounted thereonto by using said design data and shape data on the target component being processed, and calculating the height of solder for forming the fillet by dividing the product of an inputted value of thickness and the size of said opening of said mask by the obtained size of the portion of the land not having any component mounted thereonto.

6. The method of claim 5 wherein said Step C, when being carried out for a component of a specified type, includes the steps of:
reading out the height of the component identified in said Step A from a database that registers heights of components of said specified type; and
obtaining, as data on the height of solder for forming said fillet, relative height of solder with respect to the height of the component that was read out.

7. A device for photographing a substrate with fillets formed thereon while illuminating from specified directions and automatically inspecting the shape of said fillet by using a reflected image of said fillet in a generated image, said device comprising:
a database registering for each of component types a plurality of kinds of reference data for inspection corresponding to mutually different shapes of fillets in correlation with ranges in height of solder for forming fillets having corresponding shapes;
reference data setting means for setting reference data for inspection for each of components on a target substrate for inspection; and
a memory for storing said reference data for inspection set by said reference data setting means;
wherein said reference setting means includes:
component identifying means for identifying a component of which fillets are inspected and component type thereof;
land identifying means for identifying position and size of lands corresponding to said identified component which was identified by said component identifying means;
area setting means for setting a target area for inspection for inspecting a fillet for each of the lands for which position and size were identified by said land identifying means, based on the identified position and size;
data extracting means for obtaining data indicative of height of solder for forming a fillet regarding the land for which target area for inspection was set, and reading out reference data for inspection corresponding to the data obtained from the reference data for inspection of the target component registered in said database; and
registering means for registering in said memory, for the target area for inspection set by said area setting means, data required for setting said target area for inspection and the reference data for inspection read out by said data extracting means in correlation;

wherein design data of said substrate are used in the step of identifying components to be an object of fillet inspection, and said design data include data on the size of opening of mask for solder printing; and wherein said Step C further includes the steps of reading out from said design data the size of land and the size of said opening of said mask and calculating the height of solder for forming the fillet by dividing the product of an inputted value of thickness and the size of said opening of said mask by the size of said land.

8. The device of claim 7 wherein said reference data setting means sets said reference data for inspection for each of components on a target substrate for inspection by using design data of said target substrate.

* * * * *